United States Patent
Hall et al.

(10) Patent No.: US 7,276,639 B2
(45) Date of Patent: Oct. 2, 2007

(54) PROCESS AND APPARATUS FOR DETECTING A LOSS OF REACTION IN A HYDROCARBON CONVERSION REACTION

(75) Inventors: Philip Hall, Edinburgh (GB); Ian Allan Beattie Reid, London (GB); David Charles Wilson, Doune (GB)

(73) Assignee: Ineos Europe Limited, Hampshire (GB)

( * ) Notice: Subject to any disclaimer, the term of this patent is extended or adjusted under 35 U.S.C. 154(b) by 442 days.

(21) Appl. No.: 10/398,766

(22) PCT Filed: Oct. 4, 2001

(86) PCT No.: PCT/GB01/04419

§ 371 (c)(1),
(2), (4) Date: Aug. 18, 2003

(87) PCT Pub. No.: WO02/30856

PCT Pub. Date: Apr. 18, 2002

(65) Prior Publication Data

US 2004/0097774 A1 May 20, 2004

(30) Foreign Application Priority Data

Oct. 13, 2000 (GB) .................................. 0025081.1

(51) Int. Cl.
*C07C 4/02* (2006.01)
*C07C 5/373* (2006.01)
*G01N 33/00* (2006.01)
*G01N 24/00* (2006.01)

(52) U.S. Cl. ...................... 585/658; 585/652; 585/653; 436/34; 436/55; 208/DIG. 1

(58) Field of Classification Search ................ 585/652, 585/653, 658; 436/34, 55; 208/DIG. 1
See application file for complete search history.

(56) References Cited

U.S. PATENT DOCUMENTS

| 4,069,272 | A | | 1/1978 | Hutson, Jr. | |
| 4,891,464 | A | | 1/1990 | Staggs | |
| 5,905,180 | A | * | 5/1999 | Yokoyama et al. | 585/658 |
| 6,221,280 | B1 | * | 4/2001 | Anumakonda et al. | 252/372 |
| 6,258,978 | B1 | * | 7/2001 | Kitchen et al. | 560/248 |

* cited by examiner

*Primary Examiner*—Glenn Caldarola
*Assistant Examiner*—In Suk Bullock
(74) *Attorney, Agent, or Firm*—Nixon & Vanderhye

(57) ABSTRACT

A hydrocarbon conversion process such as an auto-thermal cracking process in which a hydrocarbon feed and a molecular oxygen-containing gas are contacted in a reaction zone in the presence of a catalyst to produce an outlet stream having an oxygen concentration which is at, near or above the flammable limit and in which process a loss of reaction is detected and used as a signal to activate means for mitigating the risk of explosion downstream of the reaction zone. The loss of reaction may be detected for example by a sudden increase in oxygen concentration in the outlet stream and/or a sudden drop in temperature of the outlet stream.

32 Claims, No Drawings

PROCESS AND APPARATUS FOR DETECTING A LOSS OF REACTION IN A HYDROCARBON CONVERSION REACTION

This application is the U.S. national phase of international application PCT/GB01/04419, filed 4 Oct. 2001, which designated the U.S.

The present invention relates to a process and apparatus for detecting a loss of reaction in a hydrocarbon conversion process, and in particular, for detecting a loss of reaction in an auto-thermal cracking process.

Olefins such as ethylene and propylene may be produced by the catalytic dehydrogenation or cracking of a hydrocarbon feed. In this specification, the term "cracking" will be used to embrace both these chemical reactions.

The cracking of hydrocarbons is an endothermic process. Accordingly, heat has to be consumed for the reaction to occur. In a process known as auto-thermal cracking, the heat required for cracking is generated by combusting a portion of the initial hydrocarbon feed. This is achieved by passing a reaction mixture of the hydrocarbon feed and a molecular oxygen-containing gas over a catalyst which is capable of supporting combustion beyond the fuel rich limit of flammability. The hydrocarbon feed is partially combusted, and the heat produced by the combustion reaction is used to drive the cracking of the remainder of the hydrocarbon feed to produce a gas mixture comprising olefinic hydrocarbons. An example of an auto-thermal cracking process is described in EP-A-0 332 289. The hydrocarbon feed may also comprise hydrogen.

Under typical auto-thermal reaction conditions, the amount of oxygen which is not consumed in the combustion reaction is very low, for example, below 2 vol % and is typically well below 1 vol %. Thus, the gas mixture downstream of the catalyst bed is, in general, non-flammable.

However, it has now been found that where a loss of reaction has occurred, the oxygen concentration downstream of the catalyst may rise suddenly and may rise above the flammability limit of the gas mixture. The flammability limit is defined as the highest concentration of oxygen in a mixture that will fail to sustain combustion. If the oxygen concentration exceeds this flammability limit, a fire or explosion could result. In particular, a fire or explosion could occur in downstream processing equipment. A loss of reaction may be brought about by, for example, excessive feed flows across the catalyst, operator error, catalyst failure such as deactivation of the catalyst or equipment error.

Generally, in an auto-thermal cracking process, the catalyst throughput is very high and is usually much higher than is typically used in other hydrocarbon catalytic conversion processes. Typically, the gas hourly space velocity employed in an auto-thermal cracking process is in the region of greater than 100,000 $h^{-1}$ whereas the gas hourly space velocity in catalytic hydrocarbon processes in general, is typically less than 10,000 $h^{-1}$. Thus, there exists in an auto-thermal cracking process, a greater potential to very rapidly create potentially flammable gas mixtures.

Various methods have been employed in hydrocarbon conversion reactions to avoid the presence of flammable gas mixtures thereby minimising the risk of fire or explosion and improving the safety of the process.

For example, in U.S. Pat. No. 4,069,272 which relates to oxidative dehydrogenation of hydrocarbons, the oxygen concentration in the effluent from the oxidative dehydrogenation reaction is controlled to below the combustible limit by the addition of a recycled product stream.

In U.S. Pat. No. 4,891,464 which relates to the dehydrogenation of hydrocarbons, the rate at which an oxygen-containing gas is admixed with hydrocarbons and hydrogen upstream of a catalytic oxidation reheating zone is controlled on the basis of temperature differentials across the oxidation zone and an upstream catalytic dehydrogenation zone; measuring the actual flow rate of the oxygen-containing gas and adjusting the rate of flow based upon a maximum allowable rate of flow set by selecting the lower rate of a first allowable maximum rate based on the first temperature differential and a second allowable maximum rate based upon the second temperature differential.

There is a continual need to improve the safety of chemical processes.

We have now developed a hydrocarbon oxidation process in which potentially flammable gaseous product streams may be rapidly detected and brought under control with a reduced risk of explosion.

It is among the objects of the present invention to reduce the risk of equipment failure brought about by explosions occurring in downstream equipment in hydrocarbon oxidation reactions.

Accordingly, the present invention provides a hydrocarbon conversion process in which process a hydrocarbon feed and a molecular oxygen-containing gas are contacted in a reaction zone in the presence of a catalyst to produce an outlet stream, wherein in said process the outlet stream has an oxygen concentration which is at, near or above the flammable limit and a loss of reaction is detected and used as a signal to activate means for mitigating the risk of explosion downstream of the reaction zone.

The present invention also provides an apparatus for use in a hydrocarbon conversion process in which a loss of reaction has occurred, which apparatus comprises a reaction zone having means for disposing a catalyst therein and in which reaction zone a hydrocarbon feed and a molecular oxygen-containing gas are contacted with said catalyst to produce an outlet stream having an oxygen concentration which is at, near or above the flammable limit, means for detecting said loss of reaction and means for mitigating the risk of explosion downstream of the reaction zone.

In this application the term 'outlet stream' is taken to mean the stream emerging directly from the catalyst bed of the reaction zone.

The composition of the outlet stream will vary according to the nature of the initial hydrocarbon feed and the particular reaction conditions employed.

As explained above, the flammability limit of a mixture is defined as the highest concentration of oxygen in the mixture that will fail to sustain combustion. This limit will vary according to the pressure, temperature and composition of the outlet stream. Typically, the flammability limit of the outlet stream in an auto-thermal cracking process at 1 atm pressure and 25° C. may be up to and including 34 vol % oxygen.

Where a loss in activity of the hydrocarbon conversion process occurs, due for example, to a loss in catalyst activity, equipment failure or operator error, the amount of oxygen present in the initial hydrocarbon feed may not be totally consumed by the reaction with the consequence that unconsumed oxygen builds up in the outlet stream. This build-up of oxygen in combination with other gases present in the outlet stream, such as hydrogen, can give rise to potentially flammable gas mixtures forming in the downstream processing equipment. For example, a loss of reaction in an auto-thermal cracking process can cause the oxygen concentration downstream of the catalyst to rise to the level of the oxygen concentration in the original feed (a typical oxygen feed concentration is 30 to 35, for example 33 wt % oxygen). In some hydrocarbon conversion processes, such as auto-thermal cracking, this build up of unconsumed oxygen in the outlet stream can be rapid, for example, within a few seconds.

Thus, according to another aspect of the present invention there is provided a hydrocarbon conversion process comprising:

passing a reaction mixture over a catalyst, said reaction mixture being capable of becoming flammable over said catalyst, and comprising a hydrocarbon and a molecular oxygen-containing gas, detecting a loss of reaction downstream of the catalyst within 60 seconds or less of said loss of reaction occurring.

To minimise the risk of a flammable outlet stream exploding and potentially damaging the downstream equipment, the loss of reaction is preferably detected within 60 seconds of the loss of reaction occurring, more preferably, within 20 seconds, most preferably within 10 seconds and especially within 5 seconds, such as within 1 to 3 seconds. The precise detection time will vary depending on the particular hydrocarbon conversion reaction conditions employed and the type and layout of the downstream equipment. In general, the detection time may be determined experimentally and/or calculated from the physical laws of heat flow and heat exchange. The calculations may be carried out using computational fluid dynamic (CFD) modelling. The CFD models may be validated by comparison with experimental data.

The loss of reaction may be detected by changes in temperature using a suitable temperature detector. Where a sudden loss of reaction occurs there is generally a rapid increase in oxygen concentration in the outlet stream and also a rapid drop in temperature of the outlet stream. Consequently, a drop in temperature below a threshold value is normally indicative of the oxygen concentration in the outlet stream increasing above a threshold value. The threshold temperature may be defined as the highest temperature as is possible to sustain combustion of a molecular oxygen/hydrocarbon mixture without the oxygen concentration exceeding the flammability limit of the mixture. In a hydrocarbon conversion process, such as auto-thermal cracking, the threshold temperature is typically 400° C. or less, for example, 300 to 350° C.

Suitably, a higher temperature than the threshold temperature is chosen to activate the means of mitigating the risk of explosion downstream of the reaction zone, such as in the downstream processing equipment. Suitably, this higher temperature, (hereinafter referred to as the 'trip temperature') is a temperature between the highest temperature that the oxygen/hydrocarbon reaction mixture may be heated prior to contact with the catalyst and just below the normal operating temperature of the hydrocarbon conversion process. Suitably, the trip temperature is chosen such that the means for mitigating the risk of explosion can be activated as rapidly as possible. In general, therefore, the trip temperature should be approximately equal to the lowest normal operating temperature. Thus, in an auto-thermal cracking process, the trip temperature is preferably chosen to be within the range 350° to 1000° C., more preferably, in the range 600° to 800° C., and especially in the range 7000 to 775° C.

The temperature of the outlet stream as it emerges from the catalyst bed may be detected, determined and monitored by any suitable temperature detector. Suitable temperature detectors for use in the present invention include thermocouples, resistance probes and infra-red detectors. Thermocouples detect a change in temperature as a change in voltage over a junction of dissimilar metals. Resistance probes detect a change in temperature as a change in the resistance of a metal, such as platinum, with temperature. Infra-red detectors detect a change in temperature based on the amount of emitted infra-red radiation.

Preferably, the temperature detector employed comprises one or more thermocouples. Any suitable type of thermocouple may be used in the present invention. For example, single point or multi-point thermocouples may be used. The thermocouple may be provided with a sheath for protecting the junction of the dissimilar metals of the thermocouple. Typically, the sheath will be made of metal such as grade 316 stainless steel, inconel 600, incoloy 800 or Hastelloy. The sheath may also be insulated from the junction using, for example, magnesium oxide. In a type of thermocouple known as a grounded thermocouple, the sheath is in direct contact with the junction. Grounded thermocouples are advantageous in that they generally provide fast response times to changes in temperature but suffer from the disadvantage that they may be incompatible with certain types of electrical protection systems that are sometimes used in chemical plants.

To reduce the risk of damage during use, the thermocouple may be housed in a thermowell. This has the advantage that the thermocouple can be replaced without the need to shut-down the reactor but is disadvantageous in that the thermocouple will generally be less responsive to changes in temperature. This drawback can be minimised by using thin walls for the thermowell housing. However, it is generally preferred to employ thermocouples without thermowells, so that faster response times can be achieved. Where a thermocouple is used without a thermowell, care must be taken to try and minimise the formation of void spaces in which the reaction products can be deposited and form coke.

Where more than one thermocouple is employed in the process of the present invention, the thermocouples may be of the same or different type.

Preferably, the thermocouples employed are such that a loss of reaction can be detected within 60 seconds, preferably within 20 seconds, more preferably within 10 seconds and most preferably within 5 seconds of occurring.

The number of thermocouples used and their position downstream of the catalyst bed is such that reliability of the system may be achieved. Suitably, a single thermocouple may be positioned at each of a number of locations downstream of the catalyst bed. For example, where a catalyst is mounted horizontally with the reactant process flow downwards along the axis of a cylindrical reactor, a number of thermocouples, such as three, may be placed in the same plane below the catalyst bed. Alternatively, where a catalyst bed is divided into sectors, there may be used one thermocouple per sector of catalyst bed.

Where a cooling device such as a waste heat boiler or a water quench system is used to reduce the temperature of the outlet stream, the thermocouple(s) is/are preferably positioned upstream of the cooling device such that the thermocouple reading is not affected by the cooling stream. Most preferably, the thermocouple(s) is/are positioned immediately downstream of the catalyst bed.

Each thermocouple may be hardwired to a junction box outside the reactor. The junction box may in turn be hardwired to a control room so that data generated from each thermocouple can be detected and stored in computer memory in the control room. The data generated by the thermocouples gives the operator valuable information regarding operation of the process and whether or not a loss of reaction may have occurred. Appropriate action may then be taken in response to signs of loss of reaction.

Alternatively, or in addition to detecting a loss of reaction by a change in the temperature of the outlet stream, the loss of reaction may be detected by a change in the concentration of oxygen in the outlet stream, and, in particular, an unexpected or sudden increase in the oxygen concentration in the outlet stream. Under normal operating conditions, the oxygen concentration in the outlet stream should remain substantially constant. However, where a loss of reaction has occurred, there is usually a sudden increase in the oxygen concentration of the outlet stream. Preferably, in order to minimise the risk of explosion of the oxygen/hydrocarbon mixture present in the outlet stream, the increase in the oxygen concentration of the outlet stream should be detected within 60 seconds of a loss of reaction occurring, preferably, within 20 seconds, more preferably, within 10 seconds, such as within less than 5 seconds.

The oxygen concentration of the outlet stream may be determined and monitored using any suitable technique for the compositional analysis of gaseous mixtures which enables the concentration of oxygen to be determined.

The nature of the oxygen analysis technique used may determine the location at which the outlet stream may be analysed. For example, some oxygen detectors, for example those of the paramagnetic type, may generally only be used subsequent to cooling of the outlet stream. However, such techniques, will, in general, only provide slow response times such as 1-3 minutes.

Preferably, the oxygen concentration of the outlet stream is determined and monitored below the catalyst bed in order to minimise the response time.

Preferably, the technique used is non-invasive and minimises the time delay between sampling and analysis. Preferred techniques include infra-red, near infra-red, visible or ultra-violet spectroscopic-based techniques and in particular, near infra-red or visible spectroscopy. Any suitable infra-red, near infra-red, visible or ultra-violet spectrometer may be used.

Oxygen molecules absorb visible or near infra-red light in well-known defined frequency bands. Thus, where visible or near infra-red spectroscopy is employed, a change in the oxygen concentration of the outlet stream may be determined by comparing the relative intensity of these bands in the spectrum of the transmitted visible and/or near infra-red light beam with the intensity of the bands in the deflected spectrum, that is, the spectrum obtained after the visible and/or near infra-red light has been transmitted through the outlet stream. Correction of the spectra may be necessary to eliminate the effect of any extraneous particles present in the outlet stream and/or dirty detector windows.

A preferred spectroscopic technique is based on diode laser spectroscopy. Diode laser spectroscopy is based on the selection of one single absorption line, preferably, in the near infra-red or visible spectral range for oxygen gas. The frequency of the diode laser is tuned to correspond to the single absorption line for oxygen by adjusting the temperature and driving current of the laser. The spectral width of the diode laser is considerably narrower than the spectral width of the absorption line for oxygen. By varying the diode laser current, the diode laser wavelength is scanned across the absorption line.

The oxygen molecules in the optical path between the diode laser and the detector absorb the transmitted laser light causing the intensity of the detected laser to vary as a function of wavelength. Thus, the detected shape and size of the absorption line may be used to calculate the amount of oxygen between the transmitter and the receiver.

In a preferred embodiment, the technique is carried out in the visible region of the spectrum although other wavelengths may be used. Most preferably, the wavelength employed in the visible region is 0.6 to 0.7 microns. The technique may be carried out using an apparatus comprising a transmitting diode laser and a laser detector. A suitable apparatus is manufactured under the trade mark LaserGas by Norsk Elektro Optikk A/S (Norway). Such an apparatus is particularly useful because it takes into account any dirt on the windows of the apparatus and any dust in the analysis sample by scanning from either side of the peak frequency to establish a base line for the transition of the laser.

It may be necessary to cool and/or clean the windows of any laser apparatus employed, for example, by using a purge gas which does not interfere with the absorption spectrum. Suitable purge gases include ethane, ethylene or nitrogen. Care, must also be taken to ensure that the purge gas does not mix with the gases in the outlet stream to such an extent that a loss of reaction is unable to be detected.

The visible and near infra-red spectroscopic methods described above can be used to monitor the oxygen concentration of the outlet stream in-situ. A suitable path length should be chosen, typically 1 metre, to ensure adequate detector sensitivity. This may be achieved by placing the analyser across a vessel, such as across a reactor or large pipework/ductwork.

Alternatively, for example, where a reactor has a diameter of less than 500 mm, a suitable path length may be achieved by using a sampling system. The sampling system typically comprises a tube of length 0.6 to 2 metres, such as 1 metre. The tube may be provided with a laser source at one end, and a detector at the other end. In use, a sample of the gas to be monitored is introduced into the tube through an inlet located, for example, mid-way between the ends of the tube. A laser beam is then passed through the gas sample as it flows along the length of the tube and out through outlets located adjacent the ends of the tube. Where necessary, a purge gas is employed to cool and/or clean the windows of the laser source and detector. The purge gas is introduced through the ends of the tube and flows out of the tube via the outlets located adjacent the ends of the tube. Thus, the gas in the centre of the tube comprises essentially the gas to be monitored. This ensures that any loss of reaction may be detected to the desired degree of accuracy. The windows of the detector may be mounted transverse to the tube in the centre, in the region comprising essentially the gas to be monitored.

Other methods of detecting a loss of reaction may be employed in the present invention. For example, methods may be employed to detect the levels of unreacted hydrocarbon in the outlet stream or changes in the concentration of other combustion reaction products in the outlet stream, such as water, carbon monoxide and/or carbon dioxide.

Where a loss of reaction is detected, means for mitigating the risk of explosion are activated to reduce or avoid damage to the downstream equipment. Such means will be hereinafter referred to as an emergency shut-down system or ESDS.

The detector may be linked to the ESDS by any suitable means such that the ESDS is activated on detection of a loss of reaction. For example, thermocouple(s) may be hardwired to the ESDS.

Suitably, the ESDS includes:

i) restricting or stopping the feed of the molecular oxygen-containing gas to the catalyst bed, ii) diluting the outlet stream, for example, with an inert gas, iii) restricting or stopping the flow of the outlet stream, iv) containing the outlet stream in an area of the plant that can withstand the ignition of the outlet stream.

One or more of (i) to (iv) above may be activated and employed.

The ESDS may activate the shutting-off of the oxygen supply to the reaction zone, for example, by using an appropriate valve system such as by closing one or more, typically two valves, on the oxygen supply line to the reaction zone. Preferably, a vent valve is opened between the two oxygen valves. As an alternative to a vent valve between the two oxygen valves, a valve can be opened to an inert gas, such as nitrogen, under a higher pressure than the highest oxygen pressure to give a pressurised line block to any oxygen flow. Subsequent to shutting-off the oxygen supply to the reaction zone, the hydrocarbon supply to the reaction zone is also shut-off.

The ESDS may activate the dilution of the outlet stream with a diluent to render the outlet stream non-flammable. Suitable diluents include inert gases or fuel gases. Examples of inert gases include nitrogen and $CO_2$. Examples of fuel gases include gases rich in methane such as refinery fuel gas or natural gas; hydrocarbon gases rich in ethane or propane; and vaporised liquid fuels such as diesel.

The ESDS may activate means for restricting or stopping the flow of the outlet stream from the reaction zone. This restriction or stoppage of flow may be achieved by a single valve which is capable of diverting the outlet stream, for example, to a vent or flare.

Where the flow of the outlet stream is to be diverted, it is essential that the loss of reaction is detected in sufficient time to allow the outlet stream to be diverted before it passes the diversion point. Although this criterion may be easily achieved by locating the diversion point some distance downstream of the catalyst bed, it is preferable to divert the outlet stream as soon as possible after the catalyst bed, so as to minimise the volume, and hence the energy, of potentially flammable mixtures in the plant at any time. Care should also be taken to ensure that these gases are diverted with sufficient velocity to minimise the risk of flash back. Preferably, the diversion point should be positioned such that the time taken for the outlet stream to flow from the catalyst bed to the diversion point is less than 40 seconds, more preferably, less than 20 seconds and most preferably, less than 10 seconds (as measured or calculated by CFD at the maximum flow rate of the total plant feed at the lowest operating pressure and highest operating temperature).

In addition or as an alternative to the above ESDS measures, the outlet stream may be contained in an area of the plant which is capable of withstanding the pressures of an explosion. This containment of the outlet stream may be achieved by any suitable valve system such as by closing-off one or more shut-in valves downstream of the catalyst bed. The contained outlet stream may then be rendered non-flammable and subsequently released for example, to the plant downstream of the containment area or to a flare.

To reduce the flammability of the contained outlet stream, a gas such as an inert gas, for example, nitrogen, or a fuel gas may be introduced into the containment area. The introduced gas may also enhance mixing of the outlet stream gases and may also be used to cool heated surfaces of the plant including the reactor which could give rise to ignition of the outlet stream. The containment area may be almost completely filled with the added gas.

The composition of the contained outlet stream may be adjusted to render it non-flammable. This may be achieved, for example, by adding sufficient quantities of an inert gas and/or fuel gas to the outlet stream.

As an alternative or in addition to rendering the contained outlet stream non-flammable prior to releasing it, the contained outlet stream may be released and then rendered non-flammable. This may be achieved by feeding the contained outlet stream into a vessel such as a pipe and simultaneously feeding into the vessel/pipe a sufficient quantity of an inert and/or fuel gas to render the outlet stream non-flammable.

Where the outlet stream is to be contained it is imperative that the loss of reaction is detected in sufficient time to allow the shut-in valve to be activated before the outlet stream passes the valve. This may easily be achieved by locating the shut-in valve at a sufficient distance downstream of the catalyst bed. However, it is preferable to position the shut-in valve as close to the catalyst bed as possible, so as to minimise the volume of the contained potentially flammable outlet stream. Typically, activation of the shut-in valve should occur within 20 seconds of detection of the loss of reaction, preferably, within 10 seconds and more preferably within 5 seconds (as measured or calculated by CFD at the maximum flow rate of the total plant feed at the lowest operating pressure and highest operating temperature).

The ESDS may be used in combination with other safety devices, such as permanent pilot flames, or continuous sparking devices.

In certain hydrocarbon conversion processes, such as auto-thermal cracking, a gas mixture rich in oxygen needs to be established before the catalyst can initiate the hydrocarbon conversion reaction. Thus, on start-up in such processes, it will be desirable to over-ride the detection of the loss of reaction and the means for mitigating the risk of explosion (ESDS). However, on start-up, it is still highly desirable to prevent the build-up of potentially flammable gas mixtures downstream of the catalyst bed. A preferred method of preventing a potentially flammable outlet stream is to add a diluent gas such as an inert gas or a fuel gas, below the catalyst bed, in sufficient quantities to render the outlet stream non-flammable. Typically, sufficient fuel or inert gas is added such that the concentration of oxygen in the outlet stream is less than 5% by weight. Examples of suitable inert gases are nitrogen and $CO_2$. Examples of fuel gases include gases rich in methane such as refinery fuel gas or natural gas; hydrocarbon gases rich in ethane or propane; and vaporised liquid fuels such as diesel.

The means for detecting the loss of reaction and means for mitigating the risk of explosion may be engaged prior to any removal of the diluent gas.

On start-up, the minimum velocity of the molecular oxygen-containing gas feed used must be greater than the burning velocity in order to prevent the gas mixture above the catalyst bed from igniting. The minimum velocity of the molecular oxygen-containing gas feed must also be such that the flow of the gas is even. If the flow of the gas is uneven, false trips may occur. Where false trips occur, the minimum velocity of the molecular oxygen-containing gas should be increased.

The process of the present invention may be applied to any hydrocarbon conversion process in which the oxygen concentration in a product process stream is such that the process stream is potentially flammable. For example, the process of the present invention may be applied to the production of synthesis gas (CO and H2).

Synthesis gas may be produced by catalytically reacting methane or natural gas with oxygen under suitable reaction conditions. Such conditions are well-known in the art, and are described, for example, in EP-A-0 645 344, the contents of which are hereby incorporated by reference. Suitable reaction temperatures range from 500 to 1500° C., preferably, 800 to 1200° C., for example, 900 to 1100° C. Suitable reaction pressures range between 1 and 75 bar, for example, 10 and 40 bar. Suitable catalysts include Group VIII metals such as Fe, Ru, Os, Co, Rh, Ir, Ni, Pd and Pt. Preferred catalysts comprise Ni, Rh, Pt and/or Ir.

In a preferred embodiment of the present invention, the hydrocarbon conversion process is an auto-thermal cracking process.

Accordingly, the present invention provides a process for the production of an olefin, said process comprising contacting a hydrocarbon feed and a molecular oxygen-containing gas with a catalyst, said catalyst being capable of supporting combustion beyond the fuel rich limit of flammability so as to produce an outlet stream comprising an olefin and oxygen, wherein in said process the outlet stream has an oxygen concentration which is at, near or above the flammable limit and a loss of reaction is detected and used as a signal to activate means for mitigating the risk of explosion downstream of the reaction zone.

An auto-thermal cracking process may be used to convert both liquid and gaseous hydrocarbons into olefins. Suitable liquid hydrocarbons include naphtha, gas oils, vacuum gas oils and mixtures thereof. Preferably, however, gaseous hydrocarbons such as ethane, propane, butane and mixtures thereof are employed. Suitably, the hydrocarbon is a paraffin-containing feed comprising hydrocarbons having at least two carbon atoms.

The hydrocarbon feed is mixed with any suitable molecular oxygen-containing gas. Suitably, the molecular oxygen-containing gas is molecular oxygen, air, and/or mixtures thereof. The molecular oxygen-containing gas may be mixed with an inert gas such as nitrogen, helium or argon.

Additional feed components may be included, if so desired. Suitably, methane, hydrogen, carbon monoxide, carbon dioxide or steam may be co-fed into the reactant stream.

Any molar ratio of hydrocarbon to oxygen-containing gas is suitable provided the desired olefin is produced. The preferred stoichiometric ratio of hydrocarbon to oxygen-containing gas is 5 to 16, preferably, 5 to 13.5 times, preferably, 6 to 10 times the stoichiometric ratio of hydrocarbon to oxygen-containing gas required for complete combustion of the hydrocarbon to carbon dioxide and water.

The hydrocarbon is passed over the catalyst at a gas hourly space velocity of greater than 10,000 h$^{-1}$, preferably above 20,000 h$^{-1}$ and most preferably, greater than 100,000 h$^{-1}$. It will be understood, however, that the optimum gas hourly space velocity will depend upon the pressure and nature of the feed composition.

Preferably, hydrogen is co-fed with the hydrocarbon and molecular oxygen-containing gas into the reaction zone. The molar ratio of hydrogen to molecular oxygen-containing gas can vary over any operable range provided that the desired olefin product is produced. Suitably, the molar ratio of hydrogen to molecular oxygen-containing gas is in the range 0.2 to 4, preferably, in the range 1 to 3.

Hydrogen co-feeds are advantageous because, in the presence of the catalyst, the hydrogen combusts preferentially relative to the hydrocarbon, thereby increasing the olefin selectivity of the overall process.

Preferably, the reactant mixture of hydrocarbon and molecular oxygen-containing gas (and optionally hydrogen co-feed) is preheated prior to contact with the catalyst. Generally, the reactant mixture is preheated to temperatures below the autoignition temperature of the reactant mixture.

Advantageously, a heat exchanger may be employed to preheat the reactant mixture prior to contact with the catalyst. The use of a heat exchanger may allow the reactant mixture to be heated to high preheat temperatures such as temperatures at or above the autoignition temperature of the reactant mixture. The use of high pre-heat temperatures is beneficial in that less oxygen reactant is required which leads to economic savings; Additionally, the use of high preheat temperatures can result in improved selectivity to olefin product. It has also be found that the use of high pre-heat temperatures enhances the stability of the reaction within the catalyst thereby leading to higher sustainable superficial feed velocities.

It should be understood that the autoignition temperature of a reactant mixture is dependent on pressure as well as the feed composition: it is not an absolute value. Typically, in auto-thermal cracking processes, where the hydrocarbon is ethane at a pressure of 2 atmospheres, a preheat temperature of up to 450° C. may be used.

The catalyst may be any catalyst capable of supporting combustion beyond the fuel rich limit of flammability. The catalyst may comprise a Group VIII metal as its catalytic component. Suitable Group VIII metals include platinum, palladium, ruthenium, rhodium, osmium and iridium. Rhodium, and more particularly, platinum and palladium are preferred. Typical Group VIII metal loadings range from 0.01 to 100 wt %, preferably, between 0.01 to 20 wt %, and more preferably, from 0.01 to 10 wt % based on the total dry weight of the catalyst.

Where a Group VIII catalyst is employed, it is preferably employed in combination with a catalyst promoter. The promoter may be a Group IIIA, IVA, and/or VA metal. Alternatively, the promoter may be a transition metal; the transition metal promoter being a different metal to that which may be employed as the Group VIII transition metal catalytic component.

Preferred Group IIIA metals include Al, Ga, In and Tl. Of these, Ga and In are preferred. Preferred Group IVA metals include Ge, Sn and Pb. Of these, Ge and Sn are preferred. The preferred Group VA metal is Sb. The atomic ratio of Group VIIIB metal to the Group IIIA, IVA or VA metal may be 1:0.1-50.0, preferably, 1:0.1-12.0.

Suitable metals in the transition metal series include those metals in Group IB to VIII of the Periodic Table. In particular, transition metals selected from Groups IB, IIB, VIB, VIIB and VIII of the Periodic Table are preferred. Examples of such metals include Cr, Mo, W, Fe, Ru, Os, Co, Rh, Ir, Ni, Pt, Cu, Ag, Au, Zn, Cd and Hg. Preferred transition metal promoters are Mo, Rh, Ru, Ir, Pt, Cu and Zn. The atomic ratio of Group VIII metal to transition metal promoter may be 1:0.1-50.0, preferably, 1:0.1-12.0.

Preferably, the catalyst comprises only one promoter; the promoter being selected from Group IIIA, Group IVA, Group VB and the transition metal series. For example, the catalyst may comprise a metal selected from rhodium, platinum and palladium and a promoter selected from the group consisting of Ga, In, Sn, Ge, Ag, Au or Cu. Preferred examples of such catalysts include Pt/Ga, Pt/In, Pt/Sn, Pt/Ge, Pt/Cu, Pd/Sn, Pd/Ge, Pd/Cu and Rh/Sn. The Rh, Pt or Pd may comprise between 0.01 and 5.0 wt %, preferably, between 0.01 and 2.0 wt %, and more preferably, between 0.05 and 1.0 wt % of the total weight of the catalyst. The atomic ratio of Rh, Pt or Pd to the Group IIIA, IVA or transition metal promoter may be 1:0.1-50.0, preferably, 1:0.1-12.0. For example, atomic ratios of Rh, Pt or Pd to Sn may be 1:0.1 to 50, preferably, 1:0.1-12.0, more preferably, 1:0.2-3.0 and most preferably, 1:0.5-1.5. Atomic ratios of Pt or Pd to Ge, on the other hand, may be 1:0.1 to 50, preferably, 1:0.1-12.0, and more preferably, 1:0.5-8.0. Atomic ratios of Pt or Pd to Cu may be 1:0.1-3.0, preferably, 1:0.2-2.0, and more preferably, 1:0.5-1.5.

Alternatively, the promoter may comprise at least two metals selected from Group IIIA, Group IVA and the transition metal series. For example, where the catalyst comprises platinum, the platinum may be promoted with two metals from the transition metal series, for example, palladium and copper. Such Pt/Pd/Cu catalysts may comprise palladium in an amount of 0.01 to 5 wt %, preferably, 0.01 to 2 wt %, and more preferably, 0.01 to 1 wt % based on the total weight of the dry catalyst. The atomic ratio of Pt to Pd may be 1:0.1-10.0, preferably, 1:0.5-8.0, and more preferably, 1:1.0-5.0. The atomic ratio of platinum to copper is preferably 1:0.1-3.0, more preferably, 1:0.2-2.0, and most preferably, 1:0.5-1.5.

Where the catalyst comprises platinum, it may alternatively be promoted with one transition metal, and another metal selected from Group IIIA or Group IVA of the periodic table. In such catalysts, palladium may be present in an amount of 0.01 to 5 wt %, preferably, 0.01 to 2.0 wt %, and more preferably, 0.05-1.0 wt % based on the total weight of the catalyst. The atomic ratio of Pt to Pd may be 1:0.1-10.0, preferably, 1:0.5-8.0, and more preferably, 1:1.0-5.0. The atomic ratio of Pt to the Group IIIA or IVA metal may be 1:0.1-60, preferably, 1:0.1-50.0. Preferably, the Group IIIA or IVA metal is Sn or Ge, most preferably, Sn.

For the avoidance of doubt, the Group VIII metal and promoter in the catalyst may be present in any form, for example, as a metal, or in the form of a metal compound, such as an oxide.

It should be understood that actual concentrations of metal in the catalysts tend not to be identical to the nominal concentrations employed in the preparation of the catalyst because not all the metal employed during the preparation of the catalyst actually becomes incorporated in the catalyst composition. Thus, the nominal metal concentrations may have to be varied to ensure that the desired actual metal concentrations are achieved.

The auto-thermal cracking catalyst may be unsupported, such as in the form of a metal guaze, but is preferably, supported. Any suitable support may be used such as ceramic or metal supports, but ceramic supports are generally preferred. Where ceramic supports are used, the composition of the ceramic support may be any oxide or combination of oxides that is stable at high temperatures of, for example, between 600° C. and 1200° C. The support material preferably has a low thermal expansion co-efficient, and is resistant to phase separation at high temperatures.

Suitable ceramic supports include corderite, lithium aluminium silicate (LAS), alumina ($\alpha$-$Al_2O_3$), yttria stabilised zirconia, alumina titanate, niascon, and calcium zirconyl phosphate. The ceramic supports may be wash-coated, for example, with $\gamma$-$Al_2O_3$.

The auto-thermal cracking catalyst may be prepared by any method known in the art. For example, gel methods and wet-impregnation techniques may be employed. Typically, the support is impregnated with one or more solutions comprising the metals, dried and then calcined in air. The support may be impregnated in one or more steps. Preferably, multiple impregnation steps are employed. The support is preferably dried and calcined between each impregnation, and then subjected to a final calcination, preferably, in air. The calcined support may then be reduced, for example, by heat treatment in a hydrogen atmosphere. The reaction may be suitably carried out at a catalyst exit temperature of between 600° C. and 1200° C., preferably between 850° C. and 1050° C. and most preferably, between 900° C. and 1000° C.

The catalyst employed in the auto-thermal cracking reaction may be secured in position, for example, using an intumescent material, such as Interam (manufactured by 3M).

The catalyst exit temperature may suitably be in the range 600° C. to 1200° C., preferably, in the range 850° C. to 1050° C. and, most preferably, in the range 900° C. to 1000° C.

The auto-thermal cracking process may be carried out at atmospheric or elevated pressure. Suitably, the pressure may be in the range from 0 to 2 bara, preferably 1.5 to 2 bara, for example 1.8 bara. Elevated pressures of, for example, 2 to 50 bara, may also be suitable.

Where the auto-thermal cracking process is carried out at elevated pressure, the reaction products may be quenched as they emerge from the reaction chamber to avoid further reactions taking place.

Any coke produced in the auto-thermal cracking process may be removed by mechanical means, or by using one of the decoking methods such as that described in EP-A-0 709 446, the contents of which are hereby incorporated by reference.

The present invention will now be illustrated by way of example only and with reference to the following Examples.

EXAMPLE 1

CFD modelling was employed in this Example to illustrate the effectiveness of the present invention in mitigating the risk of explosion of a potentially flammable outlet stream from an autothermal cracking process in which ethane is reacted with oxygen in the presence of a platinum based catalyst to produce an outlet stream comprising ethylene and unconsumed oxygen.

The auto-thermal cracking process is carried out in a fixed-bed reactor comprising a catalyst bed. A shut-in valve is located downstream of the catalyst bed. An outlet stream comprising the ethylene product and unconsumed oxygen passes from the catalyst bed to the shut-in valve through vessels and pipework having a total volume of 2.3 m$^3$. Approximately 25% of the vessels and/or pipework may have a temperature of as high as 350° C. whereas the rest of the vessels/pipework may only be at a temperature of 80° C. The reactor, appropriate vessels and pipework are fitted with 3 mm diameter thermocouples without thermowells. Each thermocouple is protected by an inconel 600 sheath of 0.3 mm in thickness and insulated from the junction by magnesium oxide. The sensing wire for the thermocouples has a diameter of 1 mm.

The maximum flow rate at the highest operating temperature and lowest operating pressure based on an ethane flow rate of 250 kg/h is 0.129 m3/s. This gives a time to the shut-in valve of approximately 20 seconds.

The trip temperature was set at 750° C.

The oxygen concentration of the outlet stream was controlled to a maximum of 2 vol %.

The 2D CFD model obtained from the thermocouple detector data indicated that the detection of a loss of reaction would be reached in 1.6 seconds from the loss of reaction occurring. On detection of the loss of reaction, the shut-in valve would be shut-off within 2 seconds thereby ensuring that no flammable gases would pass downstream of the shut-in valve.

A paramagnetic type oxygen detector located downstream of the liquid product recovery system, showed the final oxygen concentration in the outlet stream to be 4.8 vol %. 4.8 vol % is well below 6 vol % which is calculated to be the start of the flammable region for hydrogen and oxygen.

EXAMPLE 2

This Example illustrates the implementation of a laser based oxygen meter to detect a loss of reaction in an auto-thermal cracking process in which a hydrocarbon feed comprising ethane is contacted in a reactor with molecular oxygen in the presence of a platinum based catalyst under auto-thermal conditions to produce an outlet stream comprising ethylene and oxygen.

A sample of the outlet stream was introduced into a sampling system via a nozzle located in a dwell tube positioned just below the catalyst bed of the reactor. The sampling system comprises a tube of approximately 5 meters in length. At one end of the tube is located a diode laser and the other end of the tube is provided with a laser detector. The diode laser and laser detector are fitted with glass windows. Such a diode laser and laser detector system are manufactured by Norsk Electro Optikk A/S.

The tube is also provided with two outlets, each adjacent to each end of the tube.

The sample of the outlet stream is introduced into the tube approximately, mid-way between the ends of the tube and at a velocity of 10 m/s. A laser beam of wavelength 0.6 to 0.7 microns is passed through the outlet stream sample as it flows along the length of the tube and exits the tube via the two outlets. The outlet stream sample was then cooled prior to being mixed with the main gas stream downstream of the plant coolers.

The detection time lag of the Norsk Electro Optikk diode laser system is 2 seconds. On detection of the loss of reaction, the oxygen valve would be actuated within 1 second. Thus, a loss of reaction may be detected within 3.5 seconds. This time period is equivalent to that of the temperature detection system of Example 1 above, in which a loss of reaction may be detected within 3.6 seconds.

EXAMPLE 3

This Example illustrates start-up of an auto-thermal cracking reaction in which the loss of reaction detection means and ESDS have been disengaged to allow the catalyst to initiate the reaction. Thus, to mitigate the risk of potentially explosive gas mixtures forming downstream of the catalyst bed, a flow of nitrogen is maintained immediately below the catalyst bed.

A bed of catalyst comprising 1 wt % platinum supported on an alumina support of porosity 30 pores per inch (ex Vesuvius Hi-Tech Ceramics Inc) and of dimensions 100 mm diameter and 60 mm deep was mounted in a fixed bed metal reactor. A feed stream comprising ethane, oxygen and hydrogen was pre-heated to 180° C.

A 500 kg/h flow of nitrogen was maintained immediately below the catalyst bed to ensure a non-flammable atmosphere until reaction was established on the catalyst.

The reaction was carried out at a pressure of 1 barg.

The oxygen feed rate was limited to 25 kg/h. The reaction is typically started with 12 kg/h of oxygen but this higher feed rate of oxygen was used to stabilise the feed prior to engaging the loss of reaction detection means and ESDS.

EXAMPLE 4

This Example relates to the setting of the trip temperature in auto-thermal cracking process in which a hydrocarbon feed comprising ethane is contacted in a reactor with molecular oxygen in the presence of a platinum based catalyst under auto-thermal conditions to produce an outlet stream comprising ethylene and oxygen.

A catalyst comprising 3 wt % platinum supported on an alumina support of porosity 30 pores per inch (ex Vesuvius Hi-Tech Ceramics Inc) and of dimensions 100 mm diameter and 60 mm deep was mounted in a fixed bed metal reactor. The reactor was equipped with type K thermocouples located approximately 60 mm below the catalyst bed.

A paramagnetic type oxygen meter located downstream of the liquid product recovery system was used to determine the oxygen concentration of the outlet stream.

Ethane at a flow rate of 104 kg/h, hydrogen at a flow rate of 5.8 kg/h and 48 kg/h of oxygen were pre-heated to 180° C. and then introduced into the reactor for a period of approximately 24 hours after which the feed flow rates were halved.

After reduction of the feed flow rates, 500 kg/h of nitrogen was introduced into the reactor immediately below the catalyst bed for 1 hour to ensure a non-flammable atmosphere.

After the nitrogen purge, the oxygen flow rate was reduced at a rate of 1 kg/h per minute. When the oxygen feed rate reached approximately 8 kg/h, the temperature of the outlet stream immediately downstream of the catalyst dropped to 350° C. and the oxygen concentration in the outlet stream rose to 0.25 vol % (1.6 vol % oxygen in the absence of the nitrogen purge).

A reaction pressure of 1.6 barg was maintained throughout.

This Example shows that at 350° C. the catalyst can still support the reaction i.e substantial reaction of the oxygen is still taking place.

The invention claimed is:

1. A process for the production of an olefin1 said process comprising contacting a hydrocarbon feed and a molecular oxygen-containing gas with a catalyst, said catalyst being capable of supporting combustion beyond the fuel rich limit of flammability, wherein partial combustion of the hydrocarbon feed occurs and the heat produced by the combustion reaction drives the cracking of the remainder of the hydrocarbon feed so as to produce an outlet stream comprising an olefin and oxygen, wherein in said process the outlet stream .has an oxygen concentration which is at, near or above the flammable limit and a loss of reaction is detected and used as a signai to activate means for mitigating the risk of explosion downstream of the reaction zone, wherein the means employed for mitigating the risk of explosion is selected from one or more of the group consisting of (i) restricting or stopping the feed of molecular oxygen-containing gas to the catalyst bed, (ii) diluting the outlet stream with a diluent to render the oulet stream non-flammable, (iii) restricting or stopping the flow of the outlet stream and (iv) containing the outlet stream in an area of the plant which can withstand ignition of the outlet stream.

2. A process according to claim 1 in which the loss of reaction is detected within 60 seconds of the loss of reaction occurring.

3. A process according to claim 1 in which the loss of reaction is detected within 20 seconds of the loss of reaction occurring.

4. A process according to claim 1 which the loss of reaction is detected with a temperature detector which has a trip temperature chosen to activate the means of mitigating the risk of explosion downstream of the reaction zone, said trip temperature being in the range of 350° to 1000° C.

5. A process according to claim 4 in which the temperature detector comprises one or more thermocouples.

6. A process according to claim 5 wherein each of the one or more thermocouples is selected from the group consisting of a thermocouple without a thermowell, a thermocouple with a thin thermowell and a grounded thermocouple.

7. A process according to claim 5 wherein the thermocouple is able to detect the toss of reaction within 20 seconds of the loss of reaction occurring.

8. A process according to claim 4 wherein the temperature detector has a trip temperature in the range 600° to 800° C.

9. A process according to claim 1 in which the loss of reaction is detected by a change in the oxygen concentration in the outlet stream.

10. A process according to claim 9 in which an increase in oxygen concentration in the outlet stream is detected within 60 seconds of a loss of reaction occurring.

11. A process according to claim 9 in which the oxygen concentration is determined by a spectroscopic technique selected from infra-red, near infra-red, visible and ultraviolet spectroscopy.

12. A process according to claim 11 in which the near infra-red or visible speotroscopy employs a diode laser spectrometer.

13. A process according to claim 10 in which the wavelength employed is 0.6 to 0.7 microns.

14. A process according to claim 1 wherein the diluent is an inert gas or a fuel gas.

15. A process according to claim 1 in which the flow of the outlet stream is restricted or stopped by a valve system which diverts the flow of the outlet stream.

16. A process according to claim 15 in which the time taken for the outlet stream to flow from the catalyst bed to the diversion point is less than 40 seconds based on maximum flow rate at the lowest operating pressure and highest operating temperature.

17. A process according to claim 1 wherein the outlet stream is contained by activating a shut-in valve.

18. A process according to claim 17 wherein activation of the shut-in valve is carried out within 20 seconds of detecting the loss of reaction based on maximum flow rate at the lowest operating pressure and the highest operating temperature.

19. A process according to claim 1 wherein the contained outlet stream is rendered non-flammable.

20. A process according to claim 1 in which on start-up of the process, the detection of the loss of reaction and means for mitigating the risk of explosion is over-ridden.

21. A process according to claim 20 which further comprises adding a diluent to the outlet stream to render it non-flammable.

22. A process according to claim 21 wherein the detection of the loss of reaction and means for mitigating the risk of explosion is engaged prior to removal of the diluent from the outlet stream.

23. A process according to claim 1 wherein the hydrocarbon feed is a gaseous hydrocarbon.

24. A process according to claim 1 wherein the molecular oxygen-containing gas is selected from molecular oxygen, air and mixtures thereof.

25. A process according to claim 1 wherein hydrogen is a co-feed.

26. A process according to claim 1 in which the molar ratio of hydrocarbon feed to molecular oxygen-containing gas is 5 to 16 times the stoichiometric ratio of hydrocarbon to molecular oxygen-containing gas required for complete combustion of the hydrocarbon to carbon dioxide and water.

27. A process according to claim 1 wherein the catalyst comprises a Group VIII metal.

28. A process for the production of synthesis gas in which process a hydrocarbon feed and a molecular oxygen-containing gas are contacted in a reaction zone in the presence of a catalyst to produce an outlet stream, wherein in said process the outlet stream has an oxygen concentration which is at, near or above the flammable limit and a loss of reaction is detected and used as a signal to activate means for mitigating the risk of explosion downstream of the reaction zone, wherein the means employed for mitigating the risk of explosion is selected from one or more of the group consisting of (i) restricting or stoppina the feed of molecular oxypen-containina gas to the catalyst bed, (ii) diluting the outlet stream with a diluent to render the outlet stream non-flammable, (iii) restricting or stopping the flow of the outlet stream and (iv) containing the outlet stream in an area of the plant which can withstand ignition of the outlet stream.

29. A process according to claim 28 in which the loss of reaction is detected within 60 seconds of the loss of reaction occurring.

30. A process according to claim 28 which the loss of reaction is detected with a temperature detector which has a trip temperature chosen to activate the means of mitigating the risk of explosion downstream of the reaction zone, said trip temperature being in the range of 350° to 1000° C.

31. A process according to claim 28 in which the loss of reaction is detected by a change in the oxygen concentration in the outlet stream.

32. A process according to claim 28 in which the oxygen concentration is determined by a spectrosoopic technique selected from infra-red, near infra-red, visible and ultraviolet spectroscopy, and in which the near infra-red or visible spectroscopy employs a diode laser spectrometer.

* * * * *